(12) United States Patent
Brinkmann et al.

(10) Patent No.: US 6,521,410 B1
(45) Date of Patent: Feb. 18, 2003

(54) MUTANT OF TISSUE FACTOR PATHWAY INHIBITOR, DNA SEQUENCE AND USE FOR DETECTING THROMBOTIC DISORDERS

(75) Inventors: Thomas Brinkmann, Bielefeld (DE); Wolfgang Prohaska, Bad Oeynhausen (DE); Christian Goetting, Loehne (DE); Michael Schmidt, Bielefeld (DE)

(73) Assignee: Knut Kleesiek (DE)

( * ) Notice: Subject to any disclaimer, the term of this patent is extended or adjusted under 35 U.S.C. 154(b) by 0 days.

(21) Appl. No.: 09/763,565

(22) PCT Filed: Aug. 18, 1999

(86) PCT No.: PCT/EP99/06054

§ 371 (c)(1),
(2), (4) Date: Jun. 8, 2001

(87) PCT Pub. No.: WO00/11034

PCT Pub. Date: Mar. 2, 2000

(30) Foreign Application Priority Data

Aug. 25, 1998 (EP) .............................................. 98115957

(51) Int. Cl.⁷ ........................... C12Q 1/70; C12P 19/34; C07H 21/04

(52) U.S. Cl. .......................... 435/6; 435/91.2; 536/23.1; 536/23.5; 536/24.33

(58) Field of Search ........................... 435/6, 91.1, 91.2; 536/23.1, 24.33, 24.31; 530/350

(56) References Cited

PUBLICATIONS

Hessner et al. (Thromb Haemost (2000); 84(4): 724–25).*
Evans et al. (Thromb. Haemostasis (2000), 83(3): 511).*

* cited by examiner

*Primary Examiner*—Kenneth R. Horlick
*Assistant Examiner*—Alexander H. Spiegler
(74) *Attorney, Agent, or Firm*—Webb Ziesenheim Logsdon Orkin & Hanson, P.C.

(57) ABSTRACT

The invention relates to a novel mutant of tissue factor pathway inhibitor (TFPI) protein and its corresponding DNA sequence. The mutant can be found in humans who show or may show an increased risk of thrombotic diseases. By screening samples of human blood for said DNA or fragments of it, it is possible to predict a disposition of thrombotic disorders by which prophylactic application or measures can be initiated.

11 Claims, 2 Drawing Sheets

MUTANT OF TISSUE FACTOR PATHWAY INHIBITOR, DNA SEQUENCE AND USE FOR DETECTING THROMBOTIC DISORDERS

BACKGROUND OF THE INVENTION

1. Field of the Invention

The invention relates to a novel mutant of tissue factor pathway inhibitor (TFPI) protein and its corresponding DNA sequence. The mutant can be found in humans who show or may show an increased risk of thrombotic diseases. The DNA sequence according to this invention differs from the known TFPI coding DNA by a single nucleotide polymorphism which results in a change of one amino acid position within the known TFPI protein. By screening samples of human blood for said DNA or fragments of it, it is possible to predict a dispostion of thrombotic disorders by which prophylactic application or measures can be initiated.

2. Description of the Related Art

Tissue factor pathway inhibitor (TFPI) is an important regulator in the extrinsic blood coagulation pathway. Although the regulatory biochemical role of TFPI is evident, the clinical significance of this proteinase inhibitor remains to be elucidated. The definition of a clinical TFPI deficiency seems to be more complex than that of other coagulation inhibitors because the activity and concentration of circulating TFPI can not be considered a true measure of in vivo levels. Its determination in plasma samples by immunological methods or functional assays has been shown to be inadequate in the detection of a clinical deficiency.

TFPI is a single chain glycoprotein present in plasma in trace amounts. It was previously known as extrinsic pathway inhibitor, or lipoprotein associated coagulation inhibitor. TFPI belongs to the class of Kunitz-type proteinase inhibitors, and the mature protein contains an acidic amino-terminal end followed by three Kunitz-type inhibitory domains and a basic carboxy-terminal end. The cDNA coding for TFPI was cloned and characterized by Wun et al. (J. Biol. Chem. (1988), 263). The mature molecule consists of 276 amino acid residues, including 18 cysteins (SEQ ID NO: 2), all involved in disulfide bonds, and contains three potential N-linked glycosylation sites. The molecular weight of the polypetide backbone is about 32 kDA; the protein present in plasma runs, however, on SDS-PAGE with an apparent molecular weight of about 42 kDa, presumably due to glycosylation.

The multivalent protease inhibitor is an important regulator of the extrinsic pathway of blood coagulation through its ability to interact with the blood coagulation factor VIIa/tissue factor complex and the activated factor X via its Kunitz-type domains δ1 and δ2 (see: Girard, T. J. et al. , Nature 338, 518–520 (1989); Broze, G. J. Jr. et al.; Blood 71, 335 (1984); Rapaport, S. I. & Rao, L. V. M., Thrombosis and Haemostasis 74, 7–17 (1995); Broze, G. J. Jr. , Haemostaseologie 17, 73–77 (1997) ). There is also evidence that infusion of recombinant TFPI may protect against disseminated intravascular coagulation induced by TF or E. coli to protect against venous thrombosis and to prevent rethrombosis after successful thrombolysis in arterial thrombosis. The intravascular distribution of TFPI is complex. The mature human tissue factor pathway inhibitor protein is mainly synthesized by the vascular endothelium (Bajaj, M. S. et al. Proc. Natl. Acad. Sci. USA 88, 8869, (1990)). It has also been detected in at least four intravascular pools: bound to the endothelial cell surface, associated with lipoproteins, carrier-free within the plasma, and sequestered in platelets (Sandset, P. M. & Abildgaard, U., Haemostasis 21, 219 (1991)) A review of the regulation and role of TFPI within the extrinsic pathway system is given by Petersen at al. (Thrombosis Research, 79, 1–47 (1995)).

TFPI plays such an important role in the inhibition of the extrinsic pathway that TFPI deficiencies due to mutations in the TFPI gene should enhance the activity of the prothrombinase complex. This increases the thrombin generation and consequently the risk of venous thrombosis. Such a diminished inhibition of thrombin generation is already well known in inherited coagulation inhibitor defects that predispose to thrombosis including deficiency of antithrombin III, protein C and protein S (Dahlbäck, B. Blood 85, 607–614 (1995) ). The most prevalent inherited abnormality which is known to lead to venous thrombosis is the resistance to activated protein C caused by a single point mutation in the factor V gene (Bertina, R. M. et al., Nature 369, 64–67 (1994)).

SUMMARY OF THE INVENTION

The invention relates to a novel mutant of tissue factor pathway inhibitor (TFPI) protein and its corresponding DNA sequence. The mutant can be found in humans who show or may show an increased risk of thrombotic diseases. The DNA sequence according to this invention differs from the known TFPI coding DNA by a single nucleotide polymorphism which results in a change of one amino acid position within the known TFPI protein. It is an object of this invention to screen genomic DNA samples of human normal blood donors and thrombotic patients for alterations in the TFPI gene to assess the influence of a modified TFPI in venous thromboembolic diseases.

DESCRIPTION OF THE PREFERRED EMBODIMENTS

Figure 1:
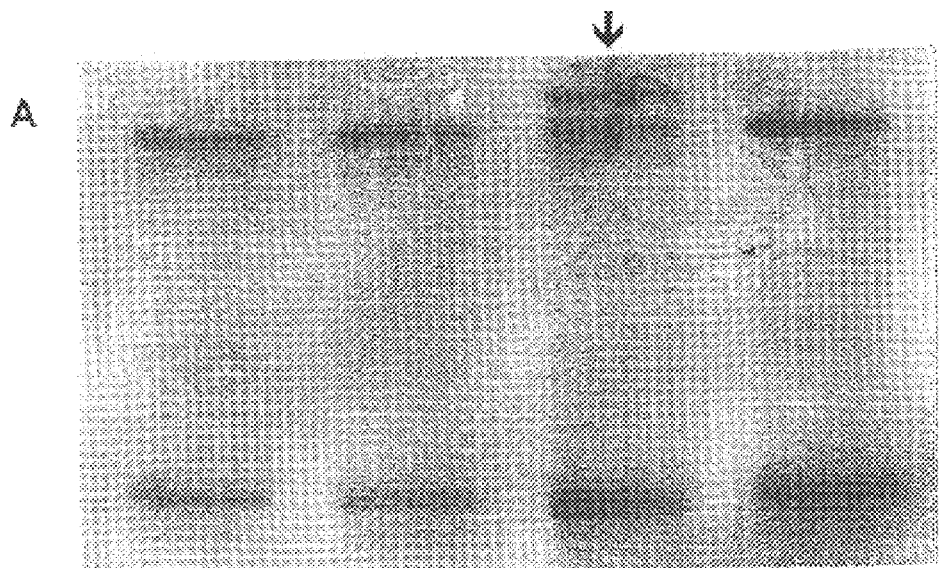
FIG. 1 depicts polymerase chain reaction and single strand conformation polymorphism results and the sequence change for the proline to leucine substitution in a TEPI variant.
Figure 1:
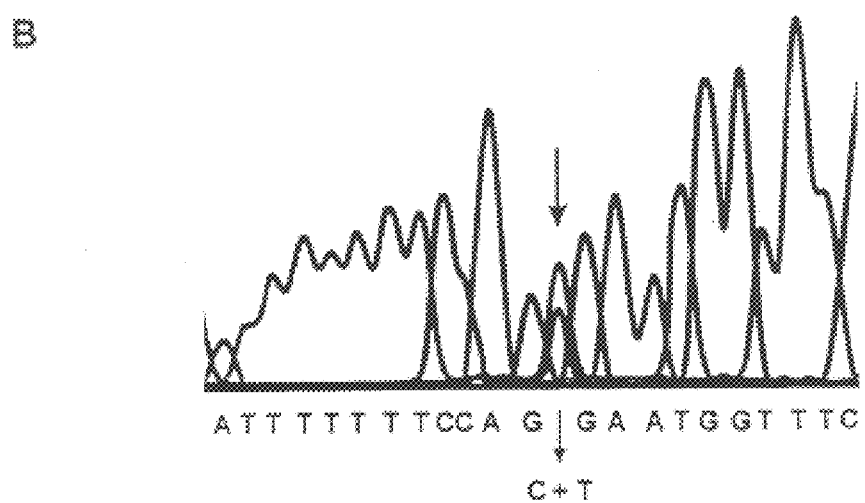
Figure 1:
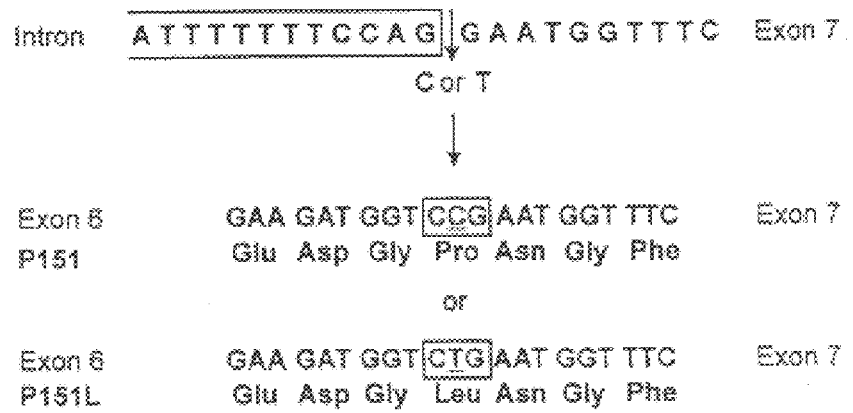

Thus it was an object of the present invention to screen genomic DNA samples of human normal blood donors and thrombotic patients for alterations in the TFPI gene to assess the influence of a modified TFPI in venous thromboembolic diseases.

Surprisingly, a single nucleotide substitution (C→T) in exon 7 of the TFPI gene could be detected, leading to a proline to leucine exchange at amino acid position 151 of the mature protein (See SEQ ID NO: 3 and SEQ ID NO: 4). Investigating the statistical significancy of this modification of TFPI it was found that said modification can be linked to a relative risk to general thrombotic disorders. However, it should be pointed out that said modification seems also to occur in human individuals showing evidently—by comparing their family health history—no increased risk to thrombotic events. Nevertheless, the finding of modified TFPI protein/DNA in blood samples of a human individual may provide an important hint for a possible disposition of said individual for thrombotic diseases. Therefore, prophylactic measures can be taken in order to prevent said diseases.

According to this invention the term "thrombotic disorders" used above and below includes all known diseases or malfunctions which can be related directly or indirectly to a permanent or temporary abnormal or pathological blood coagulation, e.g. venous thrombosis.

The modified TFPI protein or related DNA can be used as diagnostic marker to detect such a possible risk to thrombotic disorders in a patient.

Thus, it is an object of this invention to provide a DNA sequence coding for a mutant of tissue factor pathway inhibitor (TFPI) protein, wherein a proline residue at position 151 of the mature peptide (calculated from the N-terminus) is replaced by a leucine residue.

It is a further object of the invention to provide a DNA sequence comprising a DNA sequence (a) coding for a signal peptide followed by a DNA sequence (b) coding for a mutant of TFPI protein, wherein a cytosine at position 536, calculated from the start codon of the sequence (a) is replaced by a tyrosine to form a CTG codon instead of a CCG codon within the coding region of sequence (b).

Furthermore, it is an object of the invention to provide a diagnostic method to detect a disposition for thromboembolic diseases in humans by screening genomic DNA samples of human blood for a DNA sequence defined above or in the claims.

Especially, the invention relates to a diagnostic method using polymerase chain reaction (PCR) and restriction analysis by extracting total DNA from human blood samples amplifying exon 7 of the TFPI gene ( from position 536 to 628) and its previous flanking intronic region by means of suitable primers, treating the PCR products with a restriction enzyme having the recognition site ACTGG or CAGTG, and detecting the fragment length after restriction analysis or isolating and detecting the DNA defined above and in the claims.

Suitable primers according to this inventions are primers or DNA fragments which may hybridize with the corresponding regions of exon 7 of the TFPI gene, intronic flanking regions included. Therefore, as preferred embodiments, it is an object of this invention to provide a diagnostic method defined above and in the claims using the following primers (Seq. Id. No. 6, 8):

5'-TCTATTTTAATTGGCTGTAT-3' and (SEQ ID NO: 6)
5'-GCATGATAATAGTTTCCTGG-3' (SEQ ID NO; 8).

The single nucleotide polymorphism modification (C→T, CCG→CTG) in the TFPI gene at position 536 creates a new cleavage site within this region of the gene, which is not present in the original gene. This is very advantageous and can be preferably used for short evidence of such modified DNA in blood samples and, as consequence, of the abovementioned disposition for thrombotic disorders. The recognition site created by said nucleotide exchange is ACTGG (SEQ ID NO: 7) or CAGTG (Seq. ID. No. 7). Therefore, all restriction enzymes which can recognize this cleavage site are suitable to carry out the diagnostic method of the invention.

Known and suitable restriction enzymes are, for example, Bse1I, BseNI, BsrI, BsrSI, BscH1, Bst11I, BsoHI, Tsp1I and TspRI. The preferred resriction enzyme of the invention is BseNI.

Finally, it is an object of the present invention to provide the novel mutant of tissue factor pathway inhibitor (TFPI) protein wherein a proline residue at position 151 of the mature peptide (calculated from the N-terminus, without signal peptide sequence) is replaced by a leucine residue.

According to this invention it was proved the thesis that genetic variations in the TFPI gene contribute to the occurrence of hitherto unexplained cases of thrombophilia in about half of the afflicted patients. In a first screening experiment 50 unrelated individuals with a thrombotic history were investigated, who were selected to determine the genetic basis of their thrombosis (27 of them where shown to be carriers of the factor V Leiden mutation). While scanning all coding exons of the TFPI gene and the adjacent 5' and 3' intronic regions by PCR-SSCP analysis, an abnormal pattern suggesting the presence of a genetic variation, was observed in a PCR fragment from exon 7 (FIG. 1a). DNA sequencing of the fragment showing the abnormal SSCP banding pattern revealed a single heterozygous C to T mutation at nucleotide position 1 of exon 7, changing the codon $CCG^{151}$ to $CTG^{151}$ resulting in a $Pro^{151}$ to $Leu^{151}$ exchange in the amino acid of the mature protein (FIG. 1b, c; FIG. 2) (see also: van der Logt et al, *Biochemistry* 30, 1571–1577 (1991); Girard, T. J. et al.; *J. Biol. Chem.* 266, 5036–5041 (1991)).

The 536C→T transition is associated with the creation of a new recognition site for the restriction enzyme BseNI, providing a rapid means of screening further individuals for this mutation by PCR and restriction fragment length polymorphism analysis (PCR-RFLP). The primers designed for the amplification of exon 7 and the 5' and 3' flanking intronic regions were used to generate a 170 bp PCR fragment. If the nucleotide C is present at position 536, the 170 bp DNA fragment is not digestible with BseNI. However, if the nucleotide T is present at this position a 27 bp and a 143 bp restriction fragment is generated. Using this method a second set of patients was sreened with venous thrombosis (n=324) of whom 30.2% carried the factor V Leiden mutation. Another individual heterozygous for the TFPI mutation was detected. Homozygous carriers of this mutation were not found.

In order to estimate the prevalence of the 536C→T exchange in the general population, 2480 randomly chosen unrelated blood donors (age 18–60 years) were investigated by PCR-RFLP analysis.

To detect a greater number of subjects with the trait, which would allow a more precise estimation of the relative risk of those individuals to develop venous thrombosis, family members of the heterozygote blood donors and patients were investigated. In total 13 heterozygote individuals within 6 different families were found. Two of them suffered from deep vein thrombosis.

All subjects carrying the TFPI mutation were investigated for the presence of other genetic defects of clotting proteins (factor V Leiden, prothrombin 20210G→A mutation, deficiency of protein C, protein S and antithrombin III) in order to exclude the contribution of these disorders to the thromboemboiic findings. The two individuals who showed the TFPI trait and suffered from venous thrombosis had none of the additionally examined genetic disorders. Although the TFPI mutation was observed together with either the factor V Leiden mutation or the prothrombin mutation (20210G→A) in 4 members of one family, none of them had a history of thromboembolic diseases.

It is generally accepted that direct evidence for an important regulatory role of an inhibitory clotting protein requires the detection of low levels of the circulating inhibitor associated with venous thrombosis. Therefore, the TFPI activity was measured by a functional assay and the protein concentration by an immunological assay in plasma of all individuals showing the TFPI mutation. Compared with the control group (blood donors without TFPI mutation) no statistically significant differences were detected. However, existing small differences might not have been recognized, due to the low number of cases investigated so far.

Furthermore, for an interpretation of plasma TFPI levels it must be taken into consideration that compared with other coagulation inhibitors such as antithrombin III and protein C which circulate mainly as free molecules, circulating TFPI may not reflect the true measure of the total in vivo TFPI quantity. Therefore, determination of TFPI activity or protein concentration in plasma samples has been shown to be an inadequate approach to detect clinical TFPI deficiencies. The intravascular distribution of TFPI is more complex. A major pool of TFPI (about 50–80% of the total intravascular pool) is normaly bound to the endothelium, but may be released into the circulation following injection of heparin. It is also a known fact that more than 80% of the circulating TFPI is in a complex form with lipoprotein, preferentially with low density lipoprotein. However, whether this fraction of lipoprotein-associated TFPI remains active as a clotting inhibitor is still unknown. The plasma TFPI level correlates with the lipoprotein concentration, and it has been shown that patients with an inherited abetalipoproteinemia have decreased TFPI plasma concentrations but do not suffer from venous thrombosis. Therefore, the questions arises whether a deficiency of total intravascular TFPI can be detected by any of the tests used so far. (Sandset, P. M. & Bendz, B. *Thrombosis and Haemostasis* 78, 467–470 (1997)). A genetic abnormality of TFPI which promotes the development of venous thrombosis may affect different functions of the protein, such as secretion by endothelial cells, binding to the endothelial membrane, proteolysis in the vascular space, and association with lipoproteins.

So far, 13 individuals with the TFPI mutation were identified. Two of them had a history of venous thrombosis. Although the number of subjects is rather small to evaluate the risk of thrombophilia, the prevalence of venous thromboembolism in this group was compared with the prevalence in 466 blood donors who were thoroughly questioned about a possible history of venous thrombosis. 10 cases were found in this group. Statistical analysis showed a probability of 94.5% for the hypothesis that the presence of the TFPI trait is linked to thrombophilia (p=0.055; odds ratio: 5.9; 95% confidence interval: 1.0–36.5). Thus, this question remains open and can only be answered when more subjects with the TFPI mutation are available for statistical evaluation.

DESCRIPTION OF THE FIGURES

Figure 2:
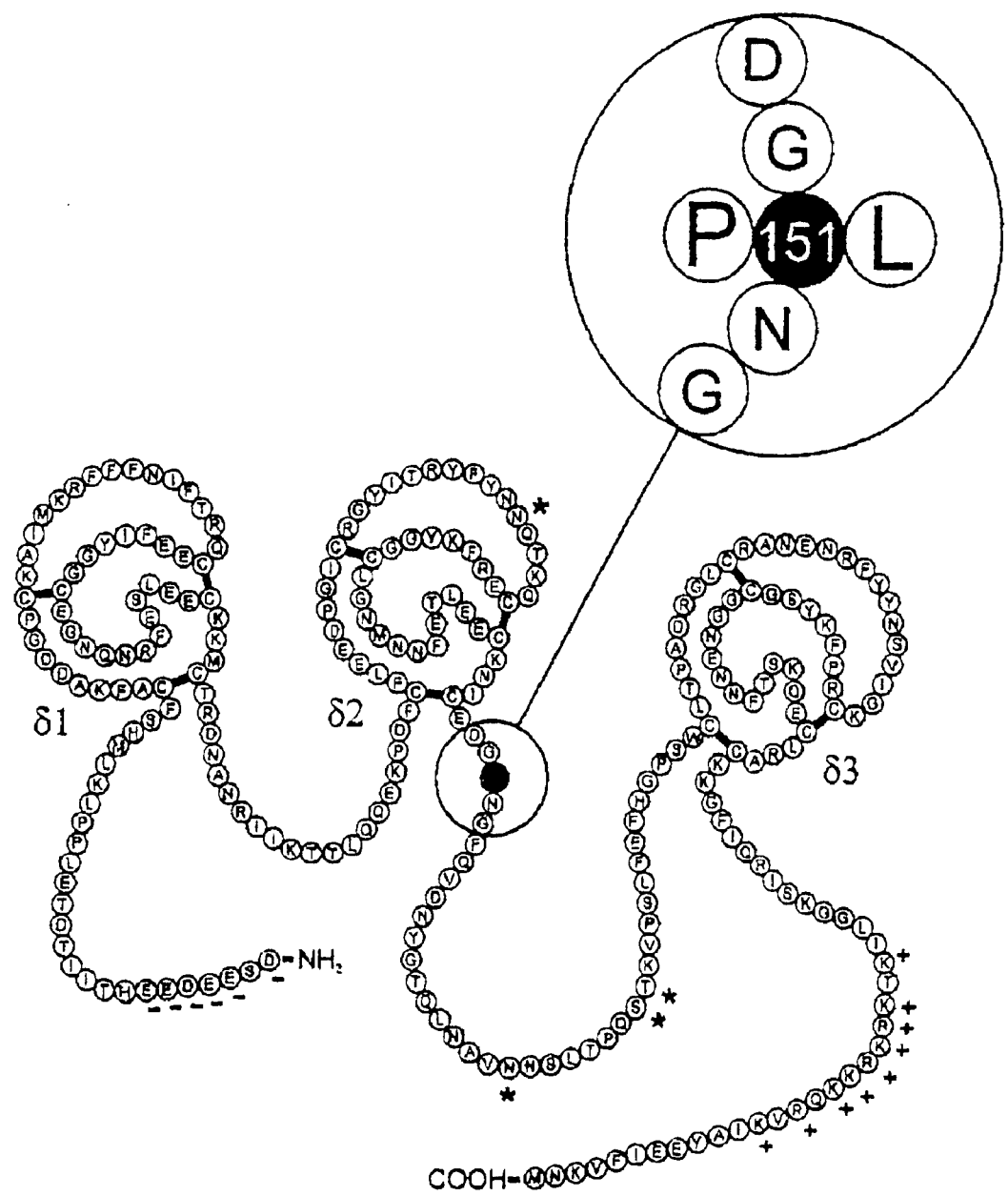
FIG. 2 is the proposed secondary structure iof the tissue factor pathway inhibitor and the position of the amino acid exchange.

FIG. 1: PCR-SSCP and sequence change for the proline to leucine substitution in a TFPI variant.

a) Single strand conformation polymorphism in exon 7 of the TFPI gene in a thrombotic patient (lane C) and nonthrombotic controls (lanes A, B, D). The arrow in lane C indicates an additional band only observed in heterozygous variants.

b) Sequencing profile of the sense strand of the PCR products obtained from total DNA from the heterozygous person identified by SSCP. The C→T transition in the nucleotide sequence, indicated by two peaks at the same position in the heterozygous probe is marked by an arrow.

c) The C→T transition at nucleotide position 1 of exon 7 results in a CCG→CTG change in the sense strand and leads to a proline to leucine substitution at position 151 of the TFPI protein.

FIG. 2: Proposed secondary structure of the tissue factor pathway inhibitor and the position of the amino acid exchange. The mature protein consists of 276 amino acids, forming three tandem Kunitz-type proteinase inhibitory domains, two connecting chains, an acidic N-terminus with negatively charged amino acids (−) and a basic carboxy-terminal end, containing a cluster of positively charged amino acids (+). Kunitz-domain δ1 has been identified as binding site for the factor VIIa/tissue factor complex, while domain δ2 binds activated factor Xa (Wesselschmidt, R. et al., *Blood* 79, 2004–2010 (1992)). Whether Kunitz-type domain δ3 binds and inhibits a specific protease is unknown. The basic carboxy-terminal end is the predicted binding site to glycosaminoglycans at the endothelial cell surface and contributes to heparin binding (Enjyoji, K.-I. et al., *Biochemistry* 34, 5725–5735 (1995)). Truncated forms of TFPI are tightly bound to low density lipoproteins and lack the distal portion of the full-length molecule including Kunitz-type domain δ53 (Broze, G. J. Jr. et al., *Blood Coag. Fibrinol.* 5, 551–559 (1994)). $Asn^{117}$ and $Asn^{167}$ are N-glycosylated, $Ser^{174}$ and $Thr^{175}$ are O-glycosylated (*) (Nakahara, T. M. et al. *Biochemistry* 35, 6450–6459 (1996)). The $Pro^{151}$ to Leu change is located near the Kunitz-type inhibitor domain δ2 within the second connecting chain (magnification).

The following examples describe the invention in more detail without restricting it.

EXAMPLE 1

Polymerase chain reaction (PCR). 374 unrelated patients with a definite history of deep vein thrombosis and 280 blood donors as a control group were investigated in this study. Total DNA of all subjects was extracted from whole blood using the QIamp Blood Kit (QIAGEN, Hilden, Germany). TFPI-exon 7 and its 5' and 3' flanking intronic regions were specifically amplified from genomic DNA by PCR (Saiki, R. K. et al., *Science* 239, 487–491 (1988)). The primers for the amplification reaction (TFPI Ex7F 5'-TCTATTTTAATTGGCTGTAT-3'(SEQ ID NO: 6), TFPI Ex7R 5'-GCATGATAATAGTTCCTGG-3'(SEQ ID NO: 8)) were derived from the genomic sequence of the TFPI gene (van der Logt et al., *Biochemistry* 30, 1571–1577 (1991)). The standard PCR included 0.1–1 μg of genomic DNA, 300 nM of each primer, 200 μM of each deoxynucleotide triphosphate, GeneAmp 10×PCR Buffer and 2.5 units of AmpliTaq DNA Polymerase (Perkin-Elmer Corporation, Foster City, Calif.) in a final volume of 50 μl. After mixing, 1 drop of mineral oil was added to each tube to prevent evaporation. Thermal cycling conditions included initial denaturation at 94° C. for 3 minutes, followed by 40 cycles of denaturing at 94° C. for 30 sec, annealing at 48° C. for 45 sec and etending at 72° C. for 45 sec. The PCR products were electrophoresed on a neutral 0.8% agarose gel and stained with ethidium bromide for inspection.

EXAMPLE 2

Single Strand Conformation Polymorphism (SSCP). Sequence variations within the amplified DNA were detected by single strand conformation polymorphism following the PCR. For SSCP analysis the amplified DNA fragments containing the coding region of exon 7 were purified using the QIAquick PCR Purification Kit (QIAGEN, Hilden, Germany). Following this procedure, the fragments were diluted 1:6 in distilled water, heated for 10 minutes at 98° C., and then quenched on ice to achieve almost complete denaturation. Electrophoresis was performed using the PhastSystem electrophoresis unit of Amersham Pharmacia Biotech (Uppsala, Sweden). Strand separation was obtained with a 12.5% Homogeneous PhastGel at a temperature of 12° C. Running conditions were: (i) Prerun: 400 V, 5.0 mA, 1.0 W, 12° C., 60 Vh; (ii) Sample application: 25 V, 5.0 mA, 1.0 W. 12° C.; 2 Vh; (iii) Main-run: 200 V, 5.0 mA, 1.0 W; 12° C., 220 Vh. Gels were silver-stained in the coloration unit of the device, following the method described by Bassam et al. (Bassam, B. J. et al, *Analyt. Biochem.* 196, 80–83 (1991)).

EXAMPLE 3

DNA-Sequence analysis of SSCP variants. The purified PCR fragments showing differences in the SSCP banding patterns were used as template for forward and reverse cycle sequencing reactions with the primers described above. The fragments were sequenced using the Applied Biosystems Incorporated (ABI) protocol for TAQ cycle sequencing with dye terminators and an automated ABI PRISM 377 DNA Sequencer (Applied Biosystems, Weiterstadt, Germany).

EXAMPLE 4

PCR-Restriction Fragment Length Polymorphism (RFLP) analysis for the determination of the TFPI 536C→T mutation. PCR was carried out as described above. The PCR product was controlled on a 0.8% agarose gel. 6 µl of the PCR product were then incubated for 1.5 h with 5 U of BseNI (MBI Fermentas, St. Leon-Rot, Germany) at 65° C. in a final volume of 20 µl without further purification. Following this, the samples were loaded onto a 2.5% agarose gel, ethidium bromide stained, and analyzed under UV-light.

EXAMPLE 5

PCR-RFLP analysis for the determination of the Factor V 1691 G→A mutation. The PCR-RFLP analysis of the factor V Leiden mutation was carried out as previously described by Beauchamp et al., using the primers Fv3 and Fv6 (Beauchamp, N. J. et al., *Brit. J. Haematol.* 88, 219–222 (1994)).

EXAMPLE 6

PCR mediated site-directed mutagenesis for the determination of the 20210 G→A transition in the prothrombin gene. The G to A transition at position 20210 in the prothrombin gene was determined after amplification with primer PTHF 5'-CGCCTGAAGTGGATACAGA-3' (SEQ ID NO: 9) and PTHR 5'-ATAGCACTGGGAGCATTGA AGC-3' (SEQ ID NO: 10). The latter was designed with a C to A substitution at position 20214 to create a restriction site for HindIII (MBI Fermentas, St. Leon-Rot, Germany) when the G to A transition at position 20210 is present in the prothrombin gene (Poort, R. S. et al., Blood 88, 3698–3703 (1996)). Restriction analysis and gel electrophoresis were carried out as described above under reaction conditions recommended by HindIII.

EXAMPLE 7

Measurement of TFPI concentration and activity in plasma samples. Total and full-length forms of TFPI, complexes with tissue factor (TF) and factor VIIa as well as binary complexes with factor Xa and quaternary complexes with TF, factor VIIa and factor Xa were quantified in plasma samples obtained from individuals heterozygous for the TFPI mutation, unaffected members of their families and blood donors, using the IMUBIND Total and Truncated TFPI ELISA Kit (American Diagnostica Inc., Greenwich, Conn.) according to the manufacturers instructions. The same plasma samples were used to determine the activity of predominantly free TFPI with the ACTICHROME TFPI Activity Assay from American Diagnostica Inc. (Greenwich, Conn.).

EXAMPLE 8

Determination of protein C and antithrombin III concentration in plasma samples. The protein C and AT III concentration in plasma samples was measured using the DADE BEHRING (Liederbach, Germany) Protein C and the Antithrombin III Chromogenic Assays according to the manufacturer's instructions.

EXAMPLE 9

Determination of protein S activity in plasma samples. The activity of the protein C cofactor was determined with the Protein S Clotting Test of Boehringer Mannheim (Mannheim, Germany). The clotting times were measured with a ball coagulometer (Amelung, Lemgo, Germany).

EXAMPLE 10

Determination of high and low density lipoprotein. To exclude plasma samples from patients with abnormal lipoprotein concentration due to association of TFPI to low density lipoprotein we determined the concentration of high and low density lipoprotein by a commercially available turbidimetric assay (Boehringer Mannheim, Mannheim, Germany).

EXAMPLE 11

Statistical analysis. The statistical analysis was performed using Chisquare test and linear logistical regression analysis for sex and age dependent calculations with the Statistical Analysis System (SAS) program, version 6.12 and Student's t-test. For statistical analysis the patients with thrombotic history were matched to the control group according to age and sex.

What is claimed is:

1. An isolated DNA sequence coding for a mutant of human tissue factor pathway inhibitor (TFPI), wherein said DNA represents a single nucleotide polymorphism exchange of the corresponding non-mutated DNA and differs from that by a thymidine (T) instead of a cytosine (C) at nucleotide position 452 of the sequence starting with the start codon coding for signal peptide-free TFPI.

2. An isolated DNA sequence coding for a mutant of human tissue factor pathway inhibitor (TFPI), wherein said mutant differs from non-mutated TFPI by a proline residue instead of a leucine residue at position 151 of the amino acid sequence of TFPI, calculated from the N-terminus of the signal-peptide free protein.

3. An isolated DNA sequence of claim 1 consisting of the sequence according to SEQ ID No: 3 starting from nucleotide position 85.

4. An isolated DNA sequence of claim 2, wherein said mutant has the amino acid sequence as depicted in SEQ ID No: 3 starting from amino acid position 1.

5. An isolated DNA sequence consisting of the DNA of claim 1 and a DNA sequence coding for a signal peptide of human TFPI.

6. An isolated DNA sequence consisting of the DNA of claim 2 and a DNA sequence coding for a signal peptide of human TFPI.

7. An isolated DNA of claim 5 consisting of the sequence according to SEQ ID No: 3, wherein said single nucleotide polymorphism exchange is at nucleotide position 536.

8. An isolated DNA of claim 6 consisting of the sequence according to SEQ ID No: 3, wherein said isolated DNA differs from the gene coding for non-mutated TFPI by a single nucleotide polymorphism exchange at nucleotide position 536.

9. A diagnostic method for detecting a potential disposition for venous thrombosis in a human subject in vitro by means of a specific mutated DNA sequence detected in genomic DNA samples of human blood, wherein said specific mutated DNA sequence (i) codes for a mutant of human tissue factor pathway inhibitor (TFPI), (ii) represents a single nucleotide polymorphism with respect to human tissue factor pathway inhibitor (TFPI), and (iii) differs from the corresponding non-mutated DNA of human tissue factor pathway inhibitor (TFPI) by a thymidine (T) instead of a cytosine (C) at nucleotide position 452 of the sequence starting with the start codon coding for signal peptide-free TFPI, or at nucleotide position 536 starting with the start codon coding of the signal peptide of TFPI having a signal peptide; said method comprising the following steps: (i) amplifying the flanking regions of exon 7 and adjcacent introns of the TFPI gene by means of polymerase chain reaction (PCR) and obtaining amplified DNA product, (ii) treating the amplified DNA obtained by the antecedent PCR step with a restriction enzyme recognizing a ACTGG or CAGTG region, (iii) analyzing the products of step (ii) for fragments cleaved by the restriction enzyme, and (iv) detecting the potential disposition for venous thrombosis in said human subject on the basis of the presence of said fragments.

10. The method of claim 9, wherein for executing PCR step (i) the following primers are used:
 (a) 5'-TCTATTTTAATTGGCTGTAT-3' (SEQ ID NO: 6), and
 (b) 5'-GCATGATAATAGTTTCCTGG-3' (SEQ ID NO: 8).

11. The method of claim 9, wherein the restriction enzyme is BseNI.

* * * * *

UNITED STATES PATENT AND TRADEMARK OFFICE
CERTIFICATE OF CORRECTION

PATENT NO. : 6,521,410 B1  Page 1 of 1
DATED : February 18, 2003
INVENTOR(S) : Thomas Brinkmann et al.

It is certified that error appears in the above-identified patent and that said Letters Patent is hereby corrected as shown below:

Column 2,
Line 2, after "(1991))" insert period -- . --.
Line 3, "at al." should read -- et al. --.

Column 3,
Line 35, "this inventions" should read -- this invention --.
Line 42, delete "and" before "(SEQ ID NO: 6)" and insert -- and -- after "(SEQ ID NO:6)"
Line 43, "(SEQ ID NO; 8)" should read -- (SEQ ID NO: 8) --.
Line 52, "(SEQ ID NO: 7)" should read -- (SEQ ID NO: 5) --.
Line 52, "(Seq. ID. No. 7)" should read -- (SEQ ID NO: 7) --.

Column 4,
Lines 49-50 "thromboemboiic" should read -- thromboembolic --.

Column 5,
Line 11, "normaly" should read -- normally --.

Column 6,
Line 15, "domain δ53" should read -- domain δ3 --.
Line 48, "etending" should read -- extending --.

Signed and Sealed this

Second Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,521,410 B1
APPLICATION NO. : 09/763565
DATED : February 18, 2003
INVENTOR(S) : Thomas Brinkmann et al.

It is certified that error appears in the above-identified patent and that said Letters Patent is hereby corrected as shown below:

<u>Title Page</u>
[75] Inventors, delete: "Thomas Brinkmann, Bielefeld (DE); Wolfgang Prohaska, Bad Oeynhausen (DE); Christian Goetting, Loehne (DE); Michael Schmidt, Bielefeld (DE)"

and insert: --Knut Kleesiek, Bad Oeynhausen (DE); Thomas Brinkmann, Bielefeld (DE); Wolfgang Prohaska, Bad Oeynhausen (DE); Christian Goetting, Loehne (DE); Michael Schmidt, Bielefeld (DE)--

Signed and Sealed this

Thirty-first Day of March, 2009

JOHN DOLL
*Acting Director of the United States Patent and Trademark Office*

SEQUENCE LISTING

```
<160> NUMBER OF SEQ ID NOS:  8

<210> SEQ ID NO 1
<211> LENGTH: 912
<212> TYPE: DNA
<213> ORGANISM: Human
<220> FEATURE:
<221> NAME/KEY: CDS
<222> LOCATION: (1)..(912)
<223> OTHER INFORMATION: TFPI protein + signal peptide
```

```
<221> NAME/KEY: sig_peptide
<222> LOCATION: (1)..(84)
<223> OTHER INFORMATION: lipoprotein-associated coagulation inhibitor
<221> NAME/KEY: mat_peptide
<222> LOCATION: (85)..(912)
<223> OTHER INFORMATION: mature TFPI

<400> SEQUENCE: 1 atg att tac aca atg aag aaa gta cat gca ctt tgg gct tct gta tgc      48
Met Ile Tyr Thr Met Lys Lys Val His Ala Leu Trp Ala Ser Val Cys
            -25                 -20                 -15 ctg ctg ctt aat ctt gcc cct gcc cct ctt aat gct gat tct gag gaa      96
Leu Leu Leu Asn Leu Ala Pro Ala Pro Leu Asn Ala Asp Ser Glu Glu
        -10                  -5                  -1   1 gat gaa gaa cac aca att atc aca gat acg gat ttg cca cca ctg aaa     144
Asp Glu Glu His Thr Ile Ile Thr Asp Thr Asp Leu Pro Pro Leu Lys
    5                   10                  15                  20 ctt atg cat tca ttt tgt gca ttc aag gcg gat gat ggc cca tgt aaa     192
Leu Met His Ser Phe Cys Ala Phe Lys Ala Asp Asp Gly Pro Cys Lys
                25                  30                  35 gca atc atg aaa aga ttt ttc ttc aat att ttc act cga cag tgc gaa     240
Ala Ile Met Lys Arg Phe Phe Phe Asn Ile Phe Thr Arg Gln Cys Glu
            40                  45                  50 gaa ttt ata tat ggg gga tgt gaa gaa aat cag aat cga ttt gaa agt     288
Glu Phe Ile Tyr Gly Gly Cys Glu Glu Asn Gln Asn Arg Phe Glu Ser
        55                  60                  65 ctg gaa gag tgc aaa aaa atg tgt aca aga gat aat gca aac agg att     336
Leu Glu Glu Cys Lys Lys Met Cys Thr Arg Asp Asn Ala Asn Arg Ile
    70                  75                  80 ata aag aca aca ttg caa caa gaa aag cca gat ttc tgc ttt ttg gaa     384
Ile Lys Thr Thr Leu Gln Gln Glu Lys Pro Asp Phe Cys Phe Leu Glu
85                  90                  95                  100 gaa gat cct gga ata tgt cga ggt tat att acc agg tat ttt tat aac     432
Glu Asp Pro Gly Ile Cys Arg Gly Tyr Ile Thr Arg Tyr Phe Tyr Asn
                105                 110                 115 aat cag aca aaa cag tgt gaa cgt ttc aag tat ggt gga tgc ctg ggc     480
Asn Gln Thr Lys Gln Cys Glu Arg Phe Lys Tyr Gly Gly Cys Leu Gly
            120                 125                 130 aat atg aac aat ttt gag aca ctg gaa gaa tgc aag aac att tgt gaa     528
Asn Met Asn Asn Phe Glu Thr Leu Glu Glu Cys Lys Asn Ile Cys Glu
        135                 140                 145 gat ggt ccg aat ggt ttc cag gtg gat aat tat gga acc cag ctc aat     576
Asp Gly Pro Asn Gly Phe Gln Val Asp Asn Tyr Gly Thr Gln Leu Asn
    150                 155                 160 gct gtg aat aac tcc ctg act ccg caa tca acc aag gtt ccc agc ctt     624
Ala Val Asn Asn Ser Leu Thr Pro Gln Ser Thr Lys Val Pro Ser Leu
165                 170                 175                 180 ttt gaa ttt cac ggt ccc tca tgg tgt ctc act cca gca gac aga gga     672
Phe Glu Phe His Gly Pro Ser Trp Cys Leu Thr Pro Ala Asp Arg Gly
                185                 190                 195 ttg tgt cgt gcc aat gag aac aga ttc tac tac aat tca gtc att ggg     720
Leu Cys Arg Ala Asn Glu Asn Arg Phe Tyr Tyr Asn Ser Val Ile Gly
            200                 205                 210 aaa tgc cgc cca ttt aag tac agt gga tgt ggg gga aat gaa aac aat     768
Lys Cys Arg Pro Phe Lys Tyr Ser Gly Cys Gly Gly Asn Glu Asn Asn
        215                 220                 225 ttt act tcc aaa caa gaa tgt ctg agg gca tgt aaa aaa ggt ttc atc     816
Phe Thr Ser Lys Gln Glu Cys Leu Arg Ala Cys Lys Lys Gly Phe Ile
    230                 235                 240 caa aga ata tca aaa gga ggc cta att aaa acc aaa aga aaa aga aag     864
Gln Arg Ile Ser Lys Gly Gly Leu Ile Lys Thr Lys Arg Lys Arg Lys
```

```
                245                 250                 255                 260
aag cag aga gtg aaa ata gca tat gaa gaa att ttt gtt aaa aat atg         912
Lys Gln Arg Val Lys Ile Ala Tyr Glu Glu Ile Phe Val Lys Asn Met
                265                 270                 275
```

<210> SEQ ID NO 2
<211> LENGTH: 304
<212> TYPE: PRT
<213> ORGANISM: Human

<400> SEQUENCE: 2

```
Met Ile Tyr Thr Met Lys Lys Val His Ala Leu Trp Ala Ser Val Cys
            -25                 -20                 -15

Leu Leu Leu Asn Leu Ala Pro Ala Pro Leu Asn Ala Asp Ser Glu Glu
        -10                  -5                  -1   1

Asp Glu Glu His Thr Ile Ile Thr Asp Thr Asp Leu Pro Pro Leu Lys
  5                  10                  15                  20

Leu Met His Ser Phe Cys Ala Phe Lys Ala Asp Asp Gly Pro Cys Lys
                 25                  30                  35

Ala Ile Met Lys Arg Phe Phe Phe Asn Ile Phe Thr Arg Gln Cys Glu
             40                  45                  50

Glu Phe Ile Tyr Gly Gly Cys Glu Gly Asn Gln Asn Arg Phe Glu Ser
             55                  60                  65

Leu Glu Glu Cys Lys Lys Met Cys Thr Arg Asp Asn Ala Asn Arg Ile
     70                  75                  80

Ile Lys Thr Thr Leu Gln Gln Glu Lys Pro Asp Phe Cys Phe Leu Glu
 85                  90                  95                 100

Glu Asp Pro Gly Ile Cys Arg Gly Tyr Ile Thr Arg Tyr Phe Tyr Asn
                105                 110                 115

Asn Gln Thr Lys Gln Cys Glu Arg Phe Lys Tyr Gly Gly Cys Leu Gly
            120                 125                 130

Asn Met Asn Asn Phe Glu Thr Leu Glu Glu Cys Lys Asn Ile Cys Glu
        135                 140                 145

Asp Gly Pro Asn Gly Phe Gln Val Asp Asn Tyr Gly Thr Gln Leu Asn
    150                 155                 160

Ala Val Asn Asn Ser Leu Thr Pro Gln Ser Thr Lys Val Pro Ser Leu
165                 170                 175                 180

Phe Glu Phe His Gly Pro Ser Trp Cys Leu Thr Pro Ala Asp Arg Gly
                185                 190                 195

Leu Cys Arg Ala Asn Glu Asn Arg Phe Tyr Tyr Asn Ser Val Ile Gly
            200                 205                 210

Lys Cys Arg Pro Phe Lys Tyr Ser Gly Cys Gly Gly Asn Glu Asn Asn
            215                 220                 225

Phe Thr Ser Lys Gln Glu Cys Leu Arg Ala Cys Lys Lys Gly Phe Ile
        230                 235                 240

Gln Arg Ile Ser Lys Gly Gly Leu Ile Lys Thr Lys Arg Lys Arg Lys
245                 250                 255                 260

Lys Gln Arg Val Lys Ile Ala Tyr Glu Glu Ile Phe Val Lys Asn Met
                265                 270                 275
```

<210> SEQ ID NO 3
<211> LENGTH: 912
<212> TYPE: DNA
<213> ORGANISM: Human
<220> FEATURE:
<221> NAME/KEY: CDS
<222> LOCATION: (1)..(912)

-continued

```
<223> OTHER INFORMATION: TFPI mutant + signal peptide
<221> NAME/KEY: mat_peptide
<222> LOCATION: (85)..(912)
<223> OTHER INFORMATION: TFPI mutant mature peptide (single nucleotide
      polymorphism)
<221> NAME/KEY: mutation
<222> LOCATION: (536)
<223> OTHER INFORMATION: mutation site: original C was replaced by T
      (Pro by Leu)

<400> SEQUENCE: 3
```

| | | | | | | | | | | | | | | | | |
|---|---|---|---|---|---|---|---|---|---|---|---|---|---|---|---|---|
| atg | att | tac | aca | atg | aag | aaa | gta | cat | gca | ctt | tgg | gct | tct | gta | tgc | 48 |
| Met | Ile | Tyr | Thr | Met | Lys | Lys | Val | His | Ala | Leu | Trp | Ala | Ser | Val | Cys | |
| | | | -25 | | | | -20 | | | | -15 | | | | | |
| ctg | ctg | ctt | aat | ctt | gcc | cct | gcc | cct | ctt | aat | gct | gat | tct | gag | gaa | 96 |
| Leu | Leu | Leu | Asn | Leu | Ala | Pro | Ala | Pro | Leu | Asn | Ala | Asp | Ser | Glu | Glu | |
| | | -10 | | | | -5 | | | | | -1 | 1 | | | | |
| gat | gaa | gaa | cac | aca | att | atc | aca | gat | acg | gat | ttg | cca | cca | ctg | aaa | 144 |
| Asp | Glu | Glu | His | Thr | Ile | Ile | Thr | Asp | Thr | Asp | Leu | Pro | Pro | Leu | Lys | |
| | 5 | | | | 10 | | | | 15 | | | | | 20 | | |
| ctt | atg | cat | tca | ttt | tgt | gca | ttc | aag | gcg | gat | gat | ggc | cca | tgt | aaa | 192 |
| Leu | Met | His | Ser | Phe | Cys | Ala | Phe | Lys | Ala | Asp | Asp | Gly | Pro | Cys | Lys | |
| | | | 25 | | | | 30 | | | | | 35 | | | | |
| gca | atc | atg | aaa | aga | ttt | ttc | ttc | aat | att | ttc | act | cga | cag | tgc | gaa | 240 |
| Ala | Ile | Met | Lys | Arg | Phe | Phe | Phe | Asn | Ile | Phe | Thr | Arg | Gln | Cys | Glu | |
| | | | 40 | | | | | 45 | | | | | 50 | | | |
| gaa | ttt | ata | tat | ggg | gga | tgt | gaa | gaa | aat | cag | aat | cga | ttt | gaa | agt | 288 |
| Glu | Phe | Ile | Tyr | Gly | Gly | Cys | Glu | Glu | Asn | Gln | Asn | Arg | Phe | Glu | Ser | |
| | | 55 | | | | | 60 | | | | | 65 | | | | |
| ctg | gaa | gag | tgc | aaa | aaa | atg | tgt | aca | aga | gat | aat | gca | aac | agg | att | 336 |
| Leu | Glu | Glu | Cys | Lys | Lys | Met | Cys | Thr | Arg | Asp | Asn | Ala | Asn | Arg | Ile | |
| | 70 | | | | | 75 | | | | | 80 | | | | | |
| ata | aag | aca | aca | ttg | caa | caa | gaa | aag | cca | gat | ttc | tgc | ttt | ttg | gaa | 384 |
| Ile | Lys | Thr | Thr | Leu | Gln | Gln | Glu | Lys | Pro | Asp | Phe | Cys | Phe | Leu | Glu | |
| 85 | | | | | 90 | | | | | 95 | | | | | 100 | |
| gaa | gat | cct | gga | ata | tgt | cga | ggt | tat | att | acc | agg | tat | ttt | tat | aac | 432 |
| Glu | Asp | Pro | Gly | Ile | Cys | Arg | Gly | Tyr | Ile | Thr | Arg | Tyr | Phe | Tyr | Asn | |
| | | | | 105 | | | | | 110 | | | | | 115 | | |
| aat | cag | aca | aaa | cag | tgt | gaa | cgt | ttc | aag | tat | ggt | gga | tgc | ctg | ggc | 480 |
| Asn | Gln | Thr | Lys | Gln | Cys | Glu | Arg | Phe | Lys | Tyr | Gly | Gly | Cys | Leu | Gly | |
| | | | 120 | | | | | 125 | | | | | 130 | | | |
| aat | atg | aac | aat | ttt | gag | aca | ctg | gaa | gaa | tgc | aag | aac | att | tgt | gaa | 528 |
| Asn | Met | Asn | Asn | Phe | Glu | Thr | Leu | Glu | Glu | Cys | Lys | Asn | Ile | Cys | Glu | |
| | | 135 | | | | | 140 | | | | | 145 | | | | |
| gat | ggt | ctg | aat | ggt | ttc | cag | gtg | gat | aat | tat | gga | acc | cag | ctc | aat | 576 |
| Asp | Gly | Leu | Asn | Gly | Phe | Gln | Val | Asp | Asn | Tyr | Gly | Thr | Gln | Leu | Asn | |
| | 150 | | | | | 155 | | | | | 160 | | | | | |
| gct | gtg | aat | aac | tcc | ctg | act | ccg | caa | tca | acc | aag | gtt | ccc | agc | ctt | 624 |
| Ala | Val | Asn | Asn | Ser | Leu | Thr | Pro | Gln | Ser | Thr | Lys | Val | Pro | Ser | Leu | |
| 165 | | | | | 170 | | | | | 175 | | | | | 180 | |
| ttt | gaa | ttt | cac | ggt | ccc | tca | tgg | tgt | ctc | act | cca | gca | gac | aga | gga | 672 |
| Phe | Glu | Phe | His | Gly | Pro | Ser | Trp | Cys | Leu | Thr | Pro | Ala | Asp | Arg | Gly | |
| | | | | 185 | | | | | 190 | | | | | 195 | | |
| ttg | tgt | cgt | gcc | aat | gag | aac | aga | ttc | tac | tac | aat | tca | gtc | att | ggg | 720 |
| Leu | Cys | Arg | Ala | Asn | Glu | Asn | Arg | Phe | Tyr | Tyr | Asn | Ser | Val | Ile | Gly | |
| | | | 200 | | | | | 205 | | | | | 210 | | | |
| aaa | tgc | cgc | cca | ttt | aag | tac | agt | gga | tgt | ggg | gga | aat | gaa | aac | aat | 768 |
| Lys | Cys | Arg | Pro | Phe | Lys | Tyr | Ser | Gly | Cys | Gly | Gly | Asn | Glu | Asn | Asn | |
| | | 215 | | | | | 220 | | | | | 225 | | | | |
| ttt | act | tcc | aaa | caa | gaa | tgt | ctg | agg | gca | tgt | aaa | aaa | ggt | ttc | atc | 816 |
| Phe | Thr | Ser | Lys | Gln | Glu | Cys | Leu | Arg | Ala | Cys | Lys | Lys | Gly | Phe | Ile | |
| | 230 | | | | | 235 | | | | | 240 | | | | | |

```
caa aga ata tca aaa gga ggc cta att aaa acc aaa aga aaa aga aag    864
Gln Arg Ile Ser Lys Gly Gly Leu Ile Lys Thr Lys Arg Lys Arg Lys
245                 250                 255                 260 aag cag aga gtg aaa ata gca tat gaa gaa att ttt gtt aaa aat atg    912
Lys Gln Arg Val Lys Ile Ala Tyr Glu Glu Ile Phe Val Lys Asn Met
                265                 270                 275
```

<210> SEQ ID NO 4
<211> LENGTH: 304
<212> TYPE: PRT
<213> ORGANISM: Human

<400> SEQUENCE: 4

```
Met Ile Tyr Thr Met Lys Lys Val His Ala Leu Trp Ala Ser Val Cys
            -25                 -20                 -15

Leu Leu Leu Asn Leu Ala Pro Ala Pro Leu Asn Ala Asp Ser Glu Glu
        -10                  -5                  -1   1

Asp Glu Glu His Thr Ile Ile Thr Asp Thr Asp Leu Pro Pro Leu Lys
  5                  10                  15                  20

Leu Met His Ser Phe Cys Ala Phe Lys Ala Asp Asp Gly Pro Cys Lys
                 25                  30                  35

Ala Ile Met Lys Arg Phe Phe Phe Asn Ile Phe Thr Arg Gln Cys Glu
             40                  45                  50

Glu Phe Ile Tyr Gly Gly Cys Glu Glu Asn Gln Asn Arg Phe Glu Ser
         55                  60                  65

Leu Glu Glu Cys Lys Lys Met Cys Thr Arg Asp Asn Ala Asn Arg Ile
     70                  75                  80

Ile Lys Thr Thr Leu Gln Gln Glu Lys Pro Asp Phe Cys Phe Leu Glu
 85                  90                  95                 100

Glu Asp Pro Gly Ile Cys Arg Gly Tyr Ile Thr Arg Tyr Phe Tyr Asn
                105                 110                 115

Asn Gln Thr Lys Gln Cys Glu Arg Phe Lys Tyr Gly Gly Cys Leu Gly
            120                 125                 130

Asn Met Asn Asn Phe Glu Thr Leu Glu Glu Cys Lys Asn Ile Cys Glu
        135                 140                 145

Asp Gly Leu Asn Gly Phe Gln Val Asp Asn Tyr Gly Thr Gln Leu Asn
    150                 155                 160

Ala Val Asn Asn Ser Leu Thr Pro Gln Ser Thr Lys Val Pro Ser Leu
165                 170                 175                 180

Phe Glu Phe His Gly Pro Ser Trp Cys Leu Thr Pro Ala Asp Arg Gly
                185                 190                 195

Leu Cys Arg Ala Asn Glu Asn Arg Phe Tyr Tyr Asn Ser Val Ile Gly
            200                 205                 210

Lys Cys Arg Pro Phe Lys Tyr Ser Gly Cys Gly Gly Asn Glu Asn Asn
        215                 220                 225

Phe Thr Ser Lys Gln Glu Cys Leu Arg Ala Cys Lys Lys Gly Phe Ile
    230                 235                 240

Gln Arg Ile Ser Lys Gly Gly Leu Ile Lys Thr Lys Arg Lys Arg Lys
245                 250                 255                 260

Lys Gln Arg Val Lys Ile Ala Tyr Glu Glu Ile Phe Val Lys Asn Met
                265                 270                 275
```

<210> SEQ ID NO 5
<211> LENGTH: 5
<212> TYPE: DNA
<213> ORGANISM: Human

-continued

```
<220> FEATURE:
<221> NAME/KEY: misc_feature
<222> LOCATION: (1)..(5)
<223> OTHER INFORMATION: restriction site

<400> SEQUENCE: 5 actgg                                                                5

<210> SEQ ID NO 6
<211> LENGTH: 20
<212> TYPE: DNA
<213> ORGANISM: Human
<220> FEATURE:
<221> NAME/KEY: primer_bind
<222> LOCATION: (1)..(20)
<223> OTHER INFORMATION: Primer

<400> SEQUENCE: 6
tctattttaa ttggctgtat                                               20

<210> SEQ ID NO 7
<211> LENGTH: 5
<212> TYPE: DNA
<213> ORGANISM: Human
<220> FEATURE:
<221> NAME/KEY: misc_feature
<222> LOCATION: (1)..(5)
<223> OTHER INFORMATION: restriction site

<400> SEQUENCE: 7 cagtg                                                                5

<210> SEQ ID NO 8
<211> LENGTH: 20
<212> TYPE: DNA
<213> ORGANISM: Human
<220> FEATURE:
<221> NAME/KEY: primer_bind
<222> LOCATION: (1)..(20)
<223> OTHER INFORMATION: Primer

<400> SEQUENCE: 8
gcatgataat agtttcctgg                                               20
```